US00PP37657P2

(12) United States Plant Patent
Hansen

(10) Patent No.: US PP37,657 P2
(45) Date of Patent: Sep. 1, 2026

(54) ***HIBISCUS* PLANT NAMED 'Coconut Cream'**

(50) Latin Name: ***Hibiscus* hybrid (L.)**
Varietal Denomination: Coconut Cream

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 19/729,049

(22) Filed: Feb. 25, 2026

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02
See application file for complete search history.

*Primary Examiner* — Kent L Bell

(57) ABSTRACT

A new and distinct cultivar of winter-hardy, herbaceous, perennial *Hibiscus* plant named 'Coconut Cream' comprising an upright, mounded habit of multiple, well-branched, basal stems producing flowers from late July to mid-September. Flowers have overlapping, heavily-rippled petals opening light yellow and becoming creamy-yellow with slightly darker veins and dark, red, shiny eye. The flower buds are greenish-yellow and the petals slightly open at the apex one to two days prior to the flower opening up flat. The foliage is typically tri-lobed, and rich olive-green with greyed-purple coloration when young and exposed to high ultraviolet light.

2 Drawing Sheets

Botanical classification: *Hibiscus* hybrid (L.).
Variety denomination: 'Coconut Cream'.

STATEMENT REGARDING PRIOR DISCLOSURES UNDER 37 CFR 1.77(B)(6)

The first offer for sale of the 'Coconut Cream' was to Centerton Nurseries, Inc. by Walters Gardens, Inc. on Mar. 20, 2025. The first disclosure was made by Walters Gardens, Inc. on Dec. 1, 2025, on the Walters Gardens, Inc. website. Walters Gardens, Inc. obtained the new plant and all information relating thereto, from the inventor. No plants of *Hibiscus* 'Coconut Cream' have been sold, in this country or anywhere in the world, by any name, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Coconut Cream' hybridized under direction of the inventor Aug. 16, 2021, at a wholesale perennial nursery in Zeeland, Michigan. The new plant is a cross between the unreleased proprietary hybrid known as 20-465-1 (not patented) as the female or seed parent and the unreleased proprietary hybrid known as 19-27-1 (not patented) as the male or pollen parent. Into the trial process the new plant was assigned the breeder code labeled 21-565-5. The parents have a complex mixture of species comprising: *moscheutos* and *coccineus*.

*Hibiscus* 'Coconut Cream' was first asexually propagated in late summer of 2022 by sterile shoot-tip tissue culture and later by shoot tip cuttings at the same nursery in Zeeland, MI. The resultant asexually propagated plants have been found to be stable and true to type in successive generations of asexual reproduction.

BRIEF SUMMARY OF THE PLANT

*Hibiscus* 'Coconut Cream' differs from its parents as well as all other hardy herbaceous *Hibiscus* known to the applicant in many traits. The most similar *Hibiscus* cultivars known to the applicant are: 'Crème Brulee' U.S. Plant Pat. No. 27,556, 'Crown Jewels' U.S. Plant Pat. No. 11,857, 'French Vanilla' U.S. Plant Pat. No. 33,181, 'Old Yella' U.S. Plant Pat. No. 13,630, and 'New Old Yella' U.S. Plant Pat. No. 23,698.

'Crème Brulee' has a less branched habit, more purple-colored foliage, flowers with smaller eyes of lighter reddish color, petals without leading edges folded under and bud apices not opening slightly days prior to opening flat. 'Crown Jewels' has a slightly taller and broader habit, and the flower color is whiter. 'French Vanilla' has a less upright habit, later to flower, slightly less rippled flower petals with a folded leading edge, the eye is a lighter red and the column base is near white, and the foliage is less greyed-purple tinted. 'Old Yella' has a taller and more open habit, the foliage is ovate and much lighter green, and the flower color is a lighter yellow. 'New Old Yella' has a larger habit with lighter green, smaller foliage with rounded bases, the flower petals are narrower, less imbricate, without the leading edge folded under, the center eye is smaller and lighter reddish color and the flower buds are not open at the apex days prior to opening flat.

The female parent plant has a taller more open habit, the foliage is dark purple foliage and the flower was a purplish-blue color. The male parent has lighter yellowish cream flowers and the foliage is less purple tinted.

*Hibiscus* 'Coconut Cream' is a unique hardy herbaceous *Hibiscus* with the following combined traits:

1. Winter-hardy compact perennial with upright, spreading, mounded habit of multiple, well-branched, basal stems;
2. Many rotate flowers opening light yellow and becoming creamy-yellow with intense sun and high temperatures;
3. Petals are overlapping and heavily rippled;
4. Flowers produced over a long period from late July to mid-September;
5. Flower bud petals are greenish-yellow and slightly open at bud apex one to two days prior to opening;
6. Primarily tri-lobed foliage of rich olive-green with greyed-purple tinting in high ultraviolet light exposure.

BRIEF DESCRIPTION OF THE DRAWINGS

The photographs of the new plant demonstrate the overall appearance of 'Coconut Cream', including the unique traits. The colors are as accurate as reasonably possible with color reproductions. Ambient light spectrum, source and direction may cause the appearance of minor variation in color. The plants in the photographs are from a four-year-old plant in an outdoor trial garden in Zeeland, Michigan.

DETAILED BOTANICAL DESCRIPTION

Figure 1:
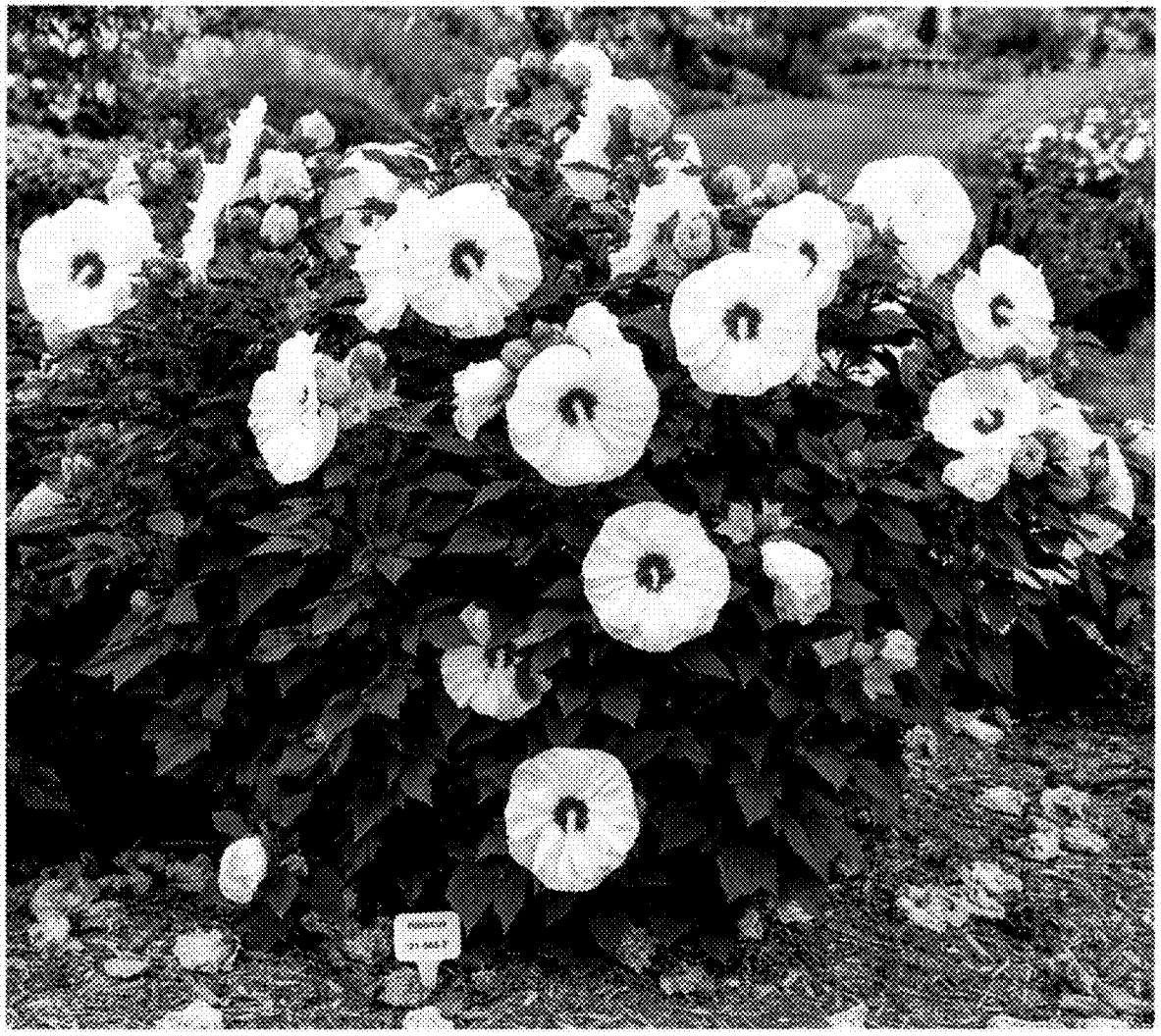
FIG. 1 shows the landscape habit of the new plant in full flower.
Figure 2:
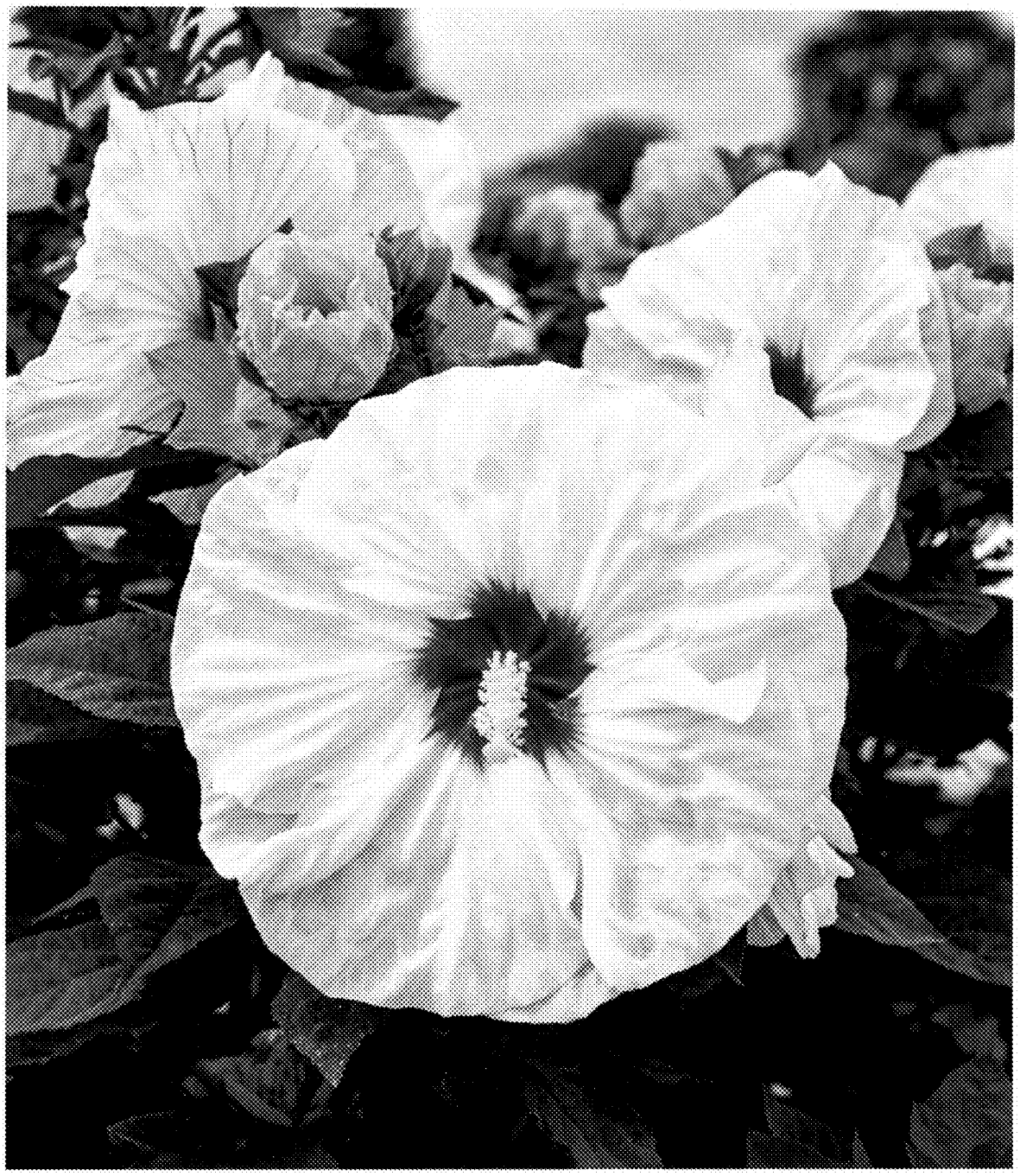
FIG. 2 shows a close-up of a bud and opened flowers.

The following descriptions and color references are based on the 2015 edition of The Royal Horticultural Society Colour Chart except where common dictionary terms are used. The new plant, *Hibiscus* 'Coconut Cream', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, MI with supplemental fertilizer and water as needed. The plants are of natural habit and were not treated with plant growth regulators, nor were they pinched at any time in the growth year.

Parentage: The female parent is 20-465-1, the male is 19-27-1;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.2 cm diameter, fleshy; root color creamy yellow nearest RHS 161D depending on soil type.

*Crop time*.—Under normal summer growing conditions 12 to 16 weeks to flower in a four-liter container from a 25 mm plug; vigor is very good.

Plant description:

*Plant habit*.—Hardy herbaceous perennial with about 16 thick, upright, heavily-branched stems producing an upright spreading mound to about 130 cm tall and about 120 cm wide; flowering from base to top of plant with up to about 26 flowers in the upper main stem and up to 60 flowers on the branches of a single stem.

*Stem*.—Terete; glabrous; glaucous; to about 128 cm tall and about 3 cm diameter at base, average about 107 cm tall and about 2.4 cm diameter at base.

*Stem color*.—Proximal main stems nearest RHS 146A with lenticular marks of nearest RHS 145C; distal main stems variable depending on light exposure, high light nearest RHS 183C, lower light between RHS 146C and RHS 146B.

*Lateral branches*.—To about 19 per stem, average about 12 per stem; terete; glabrous; glaucous; to about 20 cm long and 0.8 cm diameter at base, smaller distally.

*Lateral branch color*.—Proximally nearest a blend between RHS N138D and RHS 192B; distally nearest RHS 183C in high light to nearest RHS 146C in lower exposure.

*Internode*.—About 8 nodes per stem below branches and 22 below single flowers; average about 56 nodes per stem; internode length about 2 cm of non-pinched plant.

*Internode color*.—Same as surrounding stem.

Foliage description: Typically tri-lobed to rarely ovate distally; alternate; coarsely and irregularly crenate to dentate; apex and side lobes narrowly acute; base truncate to cordate; micro-puberulent abaxial and adaxial; moderately to deeply incised, to about 3 cm from petiole; adaxial and abaxial surfaces dull; leaf blades to about 14 cm long and about 11.6 cm across, average blade size 11.5 cm long and 8.4 cm wide; no fragrance detected;

*Foliage color*.—Young expanding leaves adaxial variable of between RHS N187A and RHS 187A and between RHS 137B and RHS 137A, abaxial between RHS 137B and RHS 137A; mature leaves adaxial nearest RHS NN137A in regions protected from high ultraviolet light and in areas of high ultraviolet light exposure between RHS N187A and RHS 187A with an undertone of nearest RHS 137A, abaxial nearest RHS 146A.

*Veins*.—Palmate; dull adaxial and abaxial; slightly applanate adaxial, costate on abaxial.

*Vein color*.—Adaxial nearest RHS N170C in proximal main veins, distally nearest RHS 148C, abaxial nearest 146C and moderately blushed with nearest RHS 183B with high ultraviolet light exposure.

*Petioles*.—Applanate adaxial to abaxial, asperous adaxial and abaxial; glabrous; straight; stiff; to about 8.5 cm long and 5 mm diameter at base, average about 6 cm long and 4 mm wide at base.

*Petiole color*.—Young and mature adaxial between RHS 146C and RHS 195B heavily blushed with RHS 187B in high light; abaxial nearest RHS 146D moderately blushed with nearest RHS 187B distally in regions of high light.

Flower description: Complete; actinomorphic; mostly outward facing; rotate; to about 18 cm across and 5 cm deep, decreasing distally; with a reddish center eye about 4.2 cm across;

*Buds one day prior to opening flat*.—Ellipsoidal with rounded apex and bluntly truncate base; sepals proximally adpressed to petals and distally flaring; to about 6 cm long and about 5 cm diameter in middle; petals not tightly closed at apices, open about 1 to 2 cm up to two days prior to petals opening flat.

*Bud color one day prior to anthesis*.—Exposed petal color nearest RHS 1C with distal veins nearest RHS 53A, calyx nearest RHS 138A with a moderate to light distal blush and veining of nearest RHS N186C.

*Inflorescence*.—Solitary; up to 75 per branched stem without pinching; nearly flat face; mostly outwardly facing.

*Flower lastingness*.—Effective for at least 6 weeks beginning late July; individually lasting one to two days.

*Flower fragrance*.—None detectable.

*Petals*.—Five; rounded, glabrous adaxial and abaxial; adaxial eye zone lustrous, remaining distal adaxial portion' and entire abaxial matte; adnate to the androecium to form a column; imbricate to about 100% overlapping at widest part (petals overlapping 100% to the petals on either side); undulation moderate; palmately veined, primary veins impressed on adaxial and slightly costate abaxial; surface moderately rippled; apex rounded with distinct basal claw and limb; margins entire, base truncate, edentate.

*Petal size*.—Average about 12.4 cm across and about 7.8 cm long, claw base about 0.8 cm across, smaller later in the flowering season; reddish eye extending about 2 cm from base with reddish veins extending distally about 0.5 cm beyond the eye.

*Petal color*.—Adaxial distal portion nearest a blend between RHS 2D and RHS 155A, the proximal 5 mm next to column nearest RHS 42A, the next distal portion before the veining nearest RHS 185A, and radiating veins nearest RHS 61C; abaxial eye nearest 155A with undertone of nearest RHS 59B, distally nearest RHS 155A with veins heavily blushed with nearest RHS 59B in distal portion with cooler weather.

*Epicalyx*.—Typically 10 to 12 per flower; linear; margin entire, glabrous; dull surface abaxial and adaxial; sharply acute apex and truncate base, arcuate upwards near apex; about 1.7 cm long and about 3 mm wide at base.

*Epicalyx color*.—Adaxial nearest RHS 146B, and abaxial nearest RHS 146A to highly blushed with RHS N186C.

*Calyx*.—Campanulate, form star-shaped hypanthium; to about 2.5 cm deep and 5.5 cm wide at apices.

*Sepals*.—Five, ovate, acute to apiculate apex; glabrous; margin entire, edentate; abaxial and adaxial surfaces matte; about 3.5 cm long, about 2.5 cm wide at slightly distal to fusion, fused in basal 1.2 cm.

*Sepal color*.—Adaxial nearest RHS 138B with veins of nearest RHS 145D; abaxial nearest RHS 138A with a moderate to light distal blush and veining of nearest RHS N186C.

*Gynoecium*.—Single; partially enclosed in column. Staminal column: glabrous and lustrous; about 3 cm long and about 12 mm diameter at base; with pistil exserted about 10 mm above top of column; Column color: without anthocyanins, nearest RHS 155D. Style: cylindrical; nearly completely enclosed in column; micro-puberulent in region above staminal column, glabrous within column; about 4 cm long, penta-furcate in about distal 5 mm, branch diameter about 1 mm; color between RHS 4C and RHS 4D. Stigma: typically five; globose, puberulent, about 3 mm in diameter and 1 mm tall; color between RHS 4A and RHS 4B. Ovary: superior; globose, longitudinally grooved; apex rounded to broadly acute, base truncate; about 6 mm across at base and about 7 mm tall; acute apex; color nearest RHS 146D.

*Androecium*.—Numerous, approximately 80 to 100. Filaments: terete; lustrous and sparsely puberulent; arcuate toward stigma; covering almost entire column; to about 4 mm long and about 0.5 mm diameter; color nearest RHS 155D. Anthers: oblong ellipsoidal; basifixed; longitudinal; about 2 mm long and 1 mm across and about 0.8 mm thick; color nearest RHS 158D. Pollen: abundant, globose, less than 0.1 mm long; color nearest RHS NN155D.

Pedicel: Terete, glabrous in distal portion and micro puberulent in proximal portion; glaucous; average length from base of sepal to abscission point about 2 cm long, from abscission point to stem node about 1 cm long; about 3 mm diameter at base; longer on early flowers and decreasing in distal flowers;

Pedicel color: Nearest RHS 146B distal abscission point, and RHS 146B with light blush of nearest RHS 183C proximal abscission point;

Peduncle: Terete; glabrous: glaucous; to about 128 cm tall and about 3 cm diameter at base, average about 107 cm tall and about 2.4 cm diameter at base;

Peduncle color: Proximal main stems nearest RHS 146A with lenticular marks of nearest RHS 145C; distal main stems nearest RHS 183C;

Fruit and seed: Not yet observed, but not tested for sterility;

Resistance: *Hibiscus* 'Coconut Cream' has not displayed any pest and disease susceptibility or resistance beyond that typical of hardy perennial *Hibiscus*.

Culture: The plant grows best with plenty of moisture.

Hardiness: At least from USDA zone 4 through 9.

I claim:

1. A new cultivar of hardy herbaceous perennial *Hibiscus* plant named 'Coconut Cream' as herein illustrated and described.

* * * * *